US006168935B1

(12) United States Patent
Yamamoto

(10) Patent No.: US 6,168,935 B1
(45) Date of Patent: Jan. 2, 2001

(54) PREPARATION OF OPTICALLY ACTIVE ALCOHOL SUBSTITUTED WITH ONE OR MORE HALOGEN ATOMS

(75) Inventor: Hiroaki Yamamoto, Tsukuba (JP)

(73) Assignee: Daicel Chemical Industries, Ltd., Osaka (JP)

( * ) Notice: Under 35 U.S.C. 154(b), the term of this patent shall be extended for 0 days.

(21) Appl. No.: 09/252,211

(22) Filed: Feb. 18, 1999

(30) Foreign Application Priority Data

Feb. 25, 1998 (JP) .................................................. 10-044014

(51) Int. Cl.$^7$ .............................. C12P 7/04; C12N 9/04; C12N 7/04

(52) U.S. Cl. ..................... 435/135; 435/156; 435/190; 435/236; 435/280

(58) Field of Search .................................. 435/135, 280, 435/156, 190, 236

(56) References Cited

U.S. PATENT DOCUMENTS

| 4,933,282 | 6/1990 | Hasegawa et al. . |
| 5,413,921 | 5/1995 | Onishi et al. . |
| 5,559,030 | 9/1996 | Matsuyama et al. . |
| 5,700,670 | 12/1997 | Yamagishi et al. . |

FOREIGN PATENT DOCUMENTS

| 0 596 490 | 5/1994 | (EP) . |
| 0 606 899 | 7/1994 | (EP) . |
| 0 635 572 | 1/1995 | (EP) . |
| 0 645 453 | 3/1995 | (EP) . |
| 61-146191 | 7/1986 | (JP) . |
| 1-211551 | 8/1989 | (JP) . |
| 1-277494 | 11/1989 | (JP) . |
| 6-38776 | 2/1994 | (JP) . |
| 7-231785 | 9/1995 | (JP) . |
| 7-231789 | 9/1995 | (JP) . |
| 2-2566960 | 10/1996 | (JP) . |
| WO98/17788 | 4/1998 | (WO) . |

OTHER PUBLICATIONS

Chemical Abstracts, vol. 112, No. 21, May 21, 1990, Abstract No. 194322.
Chemical Abstracts, vol. 110, No. 13, Mar. 27, 1989, Abstract No. 110695.

C. Wong et al., "Enzymatic vs. Fermentative Synthesis: Thermostable Glucose Dehydrogenase Catalyzed Regeneration of NAD(P)H for use in Enzymatic Synthesis", *J. Am. Chem. Soc..*, vol. 107, pp. 4028–4031, (1985).

A. Trincone et al., "Production of 4–Chloro–3–Hydroxy Ethyl Butanoate with Resting Cells of Sulfolobus Solfataricus", *Biotechnology Letters,* vol. 13, No. 1, pp. 31–34; (1991).

C. Bradshaw et al., "A Pseudomonas sp. Alcohol Dehydrogenase with Broad Substrate Specificity and Unusual Stereospecificity for Organic Synthesis", *J. Org. Chem.,* vol. 57, pp. 1526–1532, (1992).

Y. Kawai et al., "Asymmetric Reduction of β–Keto Esters with Enzyme from Bakers' Yeast", *Bull. Chem. Soc.,* vol. 67, No. 2, pp. 524–528, (1994).

K. Nakamura et al., "Asymmetric Reduction of Ketones By Glycerol Dehydrogenase From Geotricum", *Tetrahedron Letters,* vol. 29, No. 20, pp. 2453–2454, (1988).

*Primary Examiner*—Herbert J. Lilling
(74) *Attorney, Agent, or Firm*—Oliff & Berridge, PLC

(57) ABSTRACT

An optically active alcohol substituted with one or more halogen atoms, such as optically active 4-halo-3-hydroxybutyrate esters, is efficiently synthesized by using a secondary alcohol dehydrogenase and an alcohol as a substrate accompanied by the renaturing of NADH by asymmetrical reduction of a halogen-substituted ketone such as 4-haloacetoacetate esters at low temperature. By performing the reaction at low temperature, the toxicity of a halogen-substituted ketone such as 4-haloacetoacetate esters and of the optically active alcohol such as 4-halo-3-hydroxybutyrate esters, is diminished. In this way, the accumulated concentration of an optically active alcohol substituted with one or more halogen atoms, such as 4-halo-3-hydroxybutyrate esters, may be increased while retaining the high stereoselectivity of the secondary alcohol dehydrogenase.

19 Claims, No Drawings

PREPARATION OF OPTICALLY ACTIVE ALCOHOL SUBSTITUTED WITH ONE OR MORE HALOGEN ATOMS

BACKGROUND OF THE INVENTION

1. Field of the Invention

This invention relates to a method of manufacturing an optically active alcohol substituted with one or more halogen atoms which are important as an intermediate in pesticide synthesis, and in particular to a method of manufacturing optically active 4-halo-3-hydroxybutyrate esters which are useful as an intermediate in the synthesis of carnitine.

2. Description of the Related Arts

In the prior art, examples of methods of manufacturing optically active alcohols substituted with one or more halogen atoms, such as optically active 4-halo-3-hydroxybutyrate esters, include a method using an asymmetric reductive reaction of microorganisms such as baker's yeast (disclosed for example in Japanese Patent Laid-Open Publication No. Sho 61-146191 and Japanese Patent Laid-Open Publication No. Hei 6-38776), a method of asymmetric synthesis (disclosed in Japanese Patent Laid-Open Publication No. Hei 1-211551), a method of asymmetric reduction using alcohol dehydrogenase derived from 3α-hydroxysteroid dehydrogenase (Japanese Patent Laid-Open Publication No. Hei 1-277494), glycerol dehydrogenase (Tetrahedron Lett. 29,2453–2454 (1988)), alcohol dehydrogenase derived from *Thermoanaerobium brockii* or horse liver (J.Am.Chem.Soc. 107, 4028–4031 (1985)), or *Sulfolobus solfataricus* MT-4(Biotechnol. Lett.13, 31–34 (1991)), or Pseudomonas sp.(PED, J. Org. Chem. 57, 1526–1532 (1992)), and methods using a reductase dependent on nicotinamide adenine dinucleotide phosphoric acid (hereafter abbreviated as "NADPH") such as reductase from baker's yeast (Bull. Chem. Soc. Jpn. 67, 524–528 (1994) or aldehyde reductase derived from *Sporobolomyces salmonicolor* (Japanese Patent No. 2566960).

However, the alcohol produced by these methods had low optical purity and/or its concentration was low.

SUMMARY OF THE INVENTION

The inventor studied the reaction conditions required to synthesize an optically active alcohol substituted with one or more halogen atoms such as optically active 4-halo-3-hydroxybutyrate esters, using the asymmetric reduction of a halogen-substituted ketone such as 4-haloacetoacetate esters and the ability of secondary alcohol dehydrogenase to renature $NAD^+$ (oxidized nicotinamide adenine dinucleotide) to regenerate NADH (reduced nicotinamide adenine dinucleotide) which accompanies the asymmetric reductive reaction.

As a result, it was found that the toxicity and denaturing effects on enzymes of ketones comprising a halogen substituent such as 4-haloacetoacetate esters and optically active alcohols comprising a halogen substituent such as optically active 4-halo-3-hydroxybutyrate esters as substrates, could be diminished by performing the reaction at low temperature, and that by so doing, decomposition of the substrate was also suppressed. Consequently, the amount of optically active alcohols with halogen substituents which accumulated such as optically active 4-halo-3-hydroxybutyrate esters remarkably increased, and this discovery led to the present invention.

The secondary alcohol dehydrogenase of this specification is an alcohol dehydrogenase which acts as a catalyst in the oxidation of alcohols dependent on $NAD^+$ or $NADP^+$ or the reductive reaction of ketones dependent on NADH or NADPH, and it refers to secondary alcohol dehydrogenase which more preferably acts on isopropanol than n-propanol.

Specifically this invention, which uses a stereo-selective secondary alcohol dehydrogenase and an alcohol as a renaturing substrate for reduced nicotinamide adenine dinucleotide (hereafter abbreviated as NADH), provides a method of manufacturing a halogen-substituted optically active alcohol such as optically active 4-halo-3-hydroxybutyrate esters by asymmetric reduction of a halogen-substituted ketone such as 4-haloacetoacetate esters and is characterized in that it is performed at a low temperature preferably not exceeding 30° C.., more preferably not exceeding 25° C. and still more preferably not exceeding 20° C.

DETAILED DESCRIPTION OF THE INVENTION

This invention will now be described in further detail.

The stereo-selective secondary alcohol dehydrogenase of this invention may be any enzyme regardless of the source, provided it is a stereo-selective secondary alcohol dehydrogenase which has the ability to asymmetrically reduce a halogen-substituted ketone such as 4-haloacetoacetate esters, and that the amount of a halogen-substituted optically active alcohol such as 4-halo-3-hydroxybutyrate esters increases due to performing the reaction at a low temperature not exceeding 30° C. and preferably not exceeding 25° C. The secondary alcohol dehydrogenase having the following properties (disclosed in Japanese Patent Laid-Open Publication No. Hei 7-231789) are particularly useful.

(a) Functions

Oxidizes alcohols with $NAD^+$ (oxidized nicotinamide adenine dinucleotide) as coenzyme to form ketones or aldehydes, and reduces ketones or aldehydes with NADH (reduced nicotinamide adenine dinucleotide) as coenzyme to form alcohols.

(b) Substrate Specificity

Acts on aliphatic alcohols comprising aromatic substituents as substrates in an oxidative reaction, has a greater effect on secondary alcohols than on primary alcohols, preferentially oxidizes the S-form of 2-butanol, and acts on aldehydes or aliphatic ketones comprising aromatic substituents as substrates in a reductive reaction.

(c) Molecular Weight

The molecular weight is approximately 40,000 when measured by SDS-PAGE.

Herein, SDS-PAGE is an abbreviation of SDS polyacrylamide gel electrophoresis, and SDS is sodium dodecyl sulfate.

The secondary alcohol dehydrogenase derived from the Candida genus, in particular *Candida parapsilosis*, may be given as an example of a secondary alcohol dehydrogenase with these properties.

Also, the secondary alcohol dehydrogenase having the following properties (disclosed in Japanese Patent application No. Hei 8-279092) is particularly useful.

(a) Effects

Oxidizes alcohols with $NAD^+$ (oxidized nicotinamide adenine dinucleotide) as coenzyme to form ketones or aldehydes, and reduces ketones or aldehydes with NADH (reduced nicotinamide adenine dinucleotide) as coenzyme to form alcohols.

(b) Substrate Specificity

Acts on aliphatic alcohols comprising aromatic substituents as substrates in an oxidative reaction, has a greater effect on secondary alcohols than on primary alcohols, preferentially oxidizes the S-form of 1-phenylethanol, and acts on aldehydes or aliphatic ketones comprising aromatic substituents as substrates in a reductive reaction.

(c) Molecular Weight

The molecular weight is approximately 51,000 when measured by SDS-PAGE, and approximately 107,000 when measured by gel filtration.

The secondary alcohol dehydrogenase derived from the genus Geotrichum, in particular *Geotrichum candidum*, may be cited as an example of a secondary alcohol dehydrogenase having such properties.

These secondary alcohol dehydrogenases can be used in various forms such as that of the microorganism which originally contained the enzymes, the partially purified enzyme, or the purified enzyme.

It is furthermore possible to use a enzyme produced by cloning and expressing the gene which codes secondary alcohol dehydrogenase, in *Escherichia coli*, the genus Bacillus, lactic acid bacteria, coryneform bacteria, yeast such as baker's yeast, the genus Pichia or the genus Hansenula, and mold such as the genus Aspergillus. For example, recombinant cells obtained by cloning the secondary alcohol dehydrogenase gene (hereafter abbreviated as CpADH2) derived from *Candida Parapsilosis*, and culturing *Escherichia coli* bearing the expression plasmid pKK-CPA1 comprising CpADH2 gene functionally located downstream of tac promoter (disclosed in Japanese Patent Laid-Open Publication No. Hei 7-231785), is particularly to be preferred.

The one or more halogen atoms in the halogen-substituted ketone may for example be chlorine, bromine or iodine. The 4-haloacetoacetate esters mentioned herein may be a straight-chain, branched or aromatic-substituted alcohol ester such as methyl, ethyl, propyl, isopropyl, octyl or benzyl.

The alcohol used as substrate for NADH regeneration is preferably chosen with regard to specificity, stability and equilibrium, suitable examples being ethanol, methanol, isopropanol, 2-butanol, cyclohexanol, 3-pentanol, 1-phenylethanol and 2-octanol.

The reaction temperature depends on the properties of the secondary alcohol dehydrogenase used, but it should not exceed 30° C., preferably not exceed 25° C. and more preferably not exceed 20° C.

The reaction may be performed in a two-phase system comprising an organic solvent which is difficultly soluble in water, and water, and may employ a immobilized enzyme or a membrane type reactor.

DESCRIPTION OF THE ACTUAL EXAMPLES

This invention will now be described in further detail by examples, but the invention is not to be construed as being limited thereby.

Example 1

Preparation of an *Escherichia coli* Comprising Secondary Alcohol Dehydrogenase

*Escherichia coli* JM109 transformed with pKK-CPA1 which is the expression vector of secondary alcohol dehydrogenase (CpADH2) derived from *Candida Parapsilosis*, was cultured in a LB nutrient medium (1.0% polypeptone, 0.5% yeast extract, 1.0% sodium chloride, pH 7.2) at 30° C. Isopropylthiogalactoside (IPTG) was added to a final concentration of 1 mM, and culture was continued for 5 hours to give a bacillus strain containing secondary alcohol dehydrogenase.

Example 2

Effect of Reaction Temperature on 4-halo-3-hydroxybutyrate esters Synthesis 25 g of reaction mixture was prepared containing *Escherichia coli* comprising secondary alcohol dehydrogenase prepared from 25 g of culture broth, 3% of ethyl 4-chloroacetoacetate, 3.3% isopropanol, and 200mM phosphate buffer (pH 6.5). A reaction was performed for 17 hours at 30° C., 25° C., 20° C. and 15° C. The concentrations of ethyl 4-chloroacetoacetate and the product, ethyl 4-chloro-3-hydroxybutyrate, in the reaction mixture, and the optical purity of ethyl 4-chloro-3-hydroxybutyrate, were measured.

An assay of the concentrations of ethyl 4-chloroacetoacetate and ethyl 4-chloro-3-hydroxybutyrate was performed by gas chromatography under the following conditions: 2 m column (Thermon 3000 Chromosorb W, Shinwa Chemical Industries Ltd.), column temperature 150° C. and detection temperature 250° C., hydrogen flame ionization detector (FID).

Measurement of optical purity was performed by extracting ethyl 4-chloro-3-hydroxybutyrate from the reaction mixture with ethyl acetate, removing the solvent, and using high performance liquid chromatography (HPLC) with an optical resolution column (CHIRALPAK AS, Daicel Chemical Industries, Ltd.), mobile phase n-hexane/isopropanol/ethanol/cyclohexanol (92/2.5/1.2/0.25), U:J:220 nm detection, flowrate: 1 mL/min). The results measured are shown in Table 1.

TABLE 1

| Reaction temperature (° C.) | Residual amount of substrate (g/L) | Product concentration (g/L) | Optical purity (% ee) |
|---|---|---|---|
| 30 | 6.2 | 19.6 | 100.0 |
| 25 | 4.6 | 22.2 | 100.0 |
| 20 | 2.0 | 27.8 | 99.2 |
| 15 | 0.5 | 28.9 | 99.8 |

N.B.:

Substrate: ethyl 4-chloroacetoacetate (g/L)

Product: ethyl 4-chloro-3-hydroxybutyrate (g/L)

Optical purity: Optical purity of the product, units are % ee (R)

Similarly, when secondary alcohol dehydrogenase derived from the genus Geotrium was used, it was possible to increase the accumulated concentration of the product at low temperature.

This therefore provides a method of increasing the accumulated concentration of the product by performing the synthesis of optically active alcohols comprising a halogen substituent, such as optically active 4-halo-3-hydroxyethyl butyrate esters, using a stereo-selective secondary alcohol dehydrogenase at low temperature.

What is claimed is:

1. A method of manufacturing an optically active alcohol substituted with one or more halogen atoms, comprising:

a step of producing the optically active alcohol substituted with one or more halogen atoms by asymmetric reduction of a halogen-substituted ketone with a stereo-selective secondary alcohol dehydrogenase together with an alcohol for regeneration of reduced nicotinamide adenine dinucleotide, wherein the reaction of asymmetric reduction is performed at a temperature of 30° C. or less, wherein said stereo-selective secondary alcohol dehydrogenase is an enzyme having the following physicochemical properties:
(a) effects:
oxidizes alcohols with oxidized nicotinamide adenine dinucleotide as coenzyme to form ketones or aldehydes, and reduces ketones or aldehydes with reduced nicotinamide adenine dinucleotide as coenzyme to form alcohols; and
(b) substrate specificity:
acts on aliphatic alcohols comprising aromatic substituents as substrates in an oxidative reaction, has a greater effect on secondary alcohols than on primary alcohols, oxidizes the S-form of 2-butanol or the S-form of 1-phenylethanol, and acts on aldehydes or aliphatic ketones comprising aromatic substituents as substrates in a reductive reaction; and
wherein said stereo-selective secondary alcohol dehydrogenase has a molecular weight of approximately 40,000 when measured by SDS-PAGE if in a form that oxidizes the S-form of 2-butanol, or has a molecular weight of approximately 51,000 when measured by SDS-PAGE or approximately 107,000 when measured by gel filtration if in a form that oxidizes the S-form of 1-phenylethanol.

2. A method of manufacturing an optically active alcohol substituted with one or more halogen atoms according to claim 1, wherein the temperature for producing said optically active alcohol substituted with one or more halogen atoms does not exceed 25° C.

3. A method of manufacturing an optically active alcohol substituted with one or more halogen atoms according to claim 1, wherein the temperature for producing said optically active alcohol substituted with one or more halogen atoms does not exceed 20° C.

4. A method of manufacturing an optically active alcohol substituted with one or more halogen atoms according to claim 1, wherein said halogen atoms in said halogen-substituted ketone are selected from the group consisting of chlorine, bromine and iodine.

5. A method of manufacturing an optically active alcohol substituted with one or more halogen atoms according to claim 1, wherein said alcohol is at least one alcohol selected from ethanol, methanol, isopropanol, 2-butanol, cyclohexanol, 3-pentanol and 1-phenylethanol.

6. A method of manufacturing an optically active alcohol substituted with one or more halogen atoms according to claim 1, wherein said stereo-selective secondary alcohol dehydrogenase is to an enzyme expressed by cloning the gene that codes said secondary alcohol dehydrogenase using at least one of *Escherichia coli*, hay bacillus, coryneform bacillus, lactobacillus, baker's yeast, yeast and mold.

7. A method of manufacturing 4-halo-3-hydroxybutyrate esters, comprising:
a step of producing said 4-halo-3-hydroxybutyrate esters in a reaction of asymmetric reduction of 4-haloacetoacetate esters with a stereo-selective secondary alcohol dehydrogenase together with a reduced nicotinamide adenine dinucleotide and an alcohol for regeneration of reduced nicotinamide adenine dinucleotide, wherein the reaction of asymmetric reduction is performed at a temperature of 30° C. or less, wherein said stereo-selective secondary alcohol dehydrogenase is an enzyme having the following physicochemical properties:
(a) effects:
oxidizes alcohols with oxidized nicotinamide adenine dinucleotide as coenzyme to form ketones or aldehydes, and reduces ketones or aldehydes with reduced nicotinamide adenine dinucleotide as coenzyme to form alcohols;
(b) substrate specificity:
acts on aliphatic alcohols comprising aromatic substituents as substrates in an oxidative reaction, has a greater effect on secondary alcohols than on primary alcohols, oxidizes the S-form of 2-butanol, and acts on aldehydes or aliphatic ketones comprising aromatic substituents as substrates in a reductive reaction; and
(c) molecular weight:
approximately 40,000 when measured by SDS-PAGE.

8. A method of manufacturing optically active 4-halo-3-hydroxybutyrate esters according to claim 7, wherein said optically active 4-halo-3-hydroxybutyrate esters are (R)-4-halo-3-hydroxybutyrate esters.

9. A method of manufacturing optically active 4-halo-3-hydroxybutyrate esters according to claim 7, wherein the temperature for producing said optically active 4-halo-3-hydroxybutyrate esters does not exceed 25° C.

10. A method of manufacturing optically active 4-halo-3-hydroxybutyrate esters according to claim 7, wherein the temperature for producing said optically active 4-halo-3-hydroxybutyrate esters does not exceed 20° C.

11. A method of manufacturing (R)-4-halo-3-hydroxybutyrate esters according to claim 1, wherein said stereo-selective secondary alcohol dehydrogenase is a secondary alcohol dehydrogenase derived from the genus Candida.

12. A method of manufacturing (R)-4-halo-3-hydroxybutyrate esters according to claim 11, wherein said stereo-selective secondary alcohol dehydrogenase derived from the genus Candida is a secondary alcohol dehydrogenase derived from *Candida parapsilosis*.

13. A method of manufacturing (R)-4-halo-3-hydroxybutyrate esters, comprising:
a step of producing said (R)-4-halo-3-hydroxybutyrate esters in a reaction of asymmetric reduction of (R)-4-haloacetoacetate esters with a stereo-selective secondary alcohol dehydroyenase together with a reduced nicotinamide adenine dinucleotide and an alcohol for regeneration of reduced nicotinamide adenine dinucleotide, wherein the reaction of asymmetric reduction is performed at a temperature of 30° C. or less, wherein said stereo-selective secondary alcohol dehydrogenase is an enzyme having the following physicochemical properties:
(a) effects:
oxidizes alcohols with oxidized nicotinamide adenine dinucleotide as coenzyme to form ketones or aldehydes, and reduces ketones or aldehydes with reduced nicotinamide adenine dinucleotide as coenzyme to form alcohols;
(b) substrate specificity:
acts on aliphatic alcohols comprising aromatic substituents as substrates in an oxidative reaction, has a greater effect on secondary alcohols than on primary alcohols, oxidizes the S-form of 1-phenylethanol, and acts on aldehydes or aliphatic ketones comprising aromatic substituents as substrates in a reductive reaction; and
(c) molecular weight:
approximately 51,000 when measured by SDS-PAGE, and approximately 107,000 when measured by gel filtration.

14. A method of manufacturing (R)-4-halo-3-hydroxybutyrate esters according to claim 13, wherein said stereo-selective secondary alcohol dehydrogenase is a secondary alcohol dehydrogenase derived from the genus Geotrichum.

15. A method of manufacturing (R)-4-halo-3-hydroxybutyrate esters according to claim 14, wherein said stereo-selective secondary alcohol dehydrogenase derived from the genus Geotrichum is a secondary alcohol dehydrogenase derived from *Geotrichum candidum*.

16. A method of manufacturing optically active 4-halo-3-hydroxybutyrate esters according to claim 7, wherein said one or more halogen atoms in said haloacetoacetate are selected from the group consisting of chlorine, bromine and iodine.

17. A method of manufacturing optically active 4-halo-3-hydroxybutyrate esters according to claim 7, wherein the ester group in said 4-halo-3-hydroxybutyrate esters is a straight-chain or branched alkyl group, or an aromatic-substituted group.

18. A method of manufacturing optically active 4-halo-3-hydroxybutyrate esters according to claim 7, wherein said alcohol is at least one alcohol selected from ethanol, methanol, isopropanol, 2-butanol, cyclohexanol, 3-pentanol and 1-phenylethanol.

19. A method of manufacturing 4-halo-3-hydroxybutyrate esters according to claim 7, wherein said stereo-selective secondary alcohol dehydrogenase is an enzyme expressed by cloning the gene that codes said secondary alcohol dehydrogenase using at least one of *Escherichia coli*, hay bacillus, coryneform bacillus, lactobacillus, baker's yeast, yeast and mold.

* * * * *